United States Patent
Zielinski et al.

(10) Patent No.: US 7,179,841 B2
(45) Date of Patent: Feb. 20, 2007

(54) STABILIZED ASCORBIC ACID COMPOSITIONS AND METHODS THEREFOR

(75) Inventors: Jan E. Zielinski, Vista, CA (US); Sheldon R. Pinnell, Durham, NC (US)

(73) Assignee: L'Oreal USA Creative, Inc., New York, NY (US)

( * ) Notice: Subject to any disclaimer, the term of this patent is extended or adjusted under 35 U.S.C. 154(b) by 72 days.

(21) Appl. No.: 11/032,931

(22) Filed: Jan. 11, 2005

(65) Prior Publication Data

US 2005/0154054 A1    Jul. 14, 2005

Related U.S. Application Data

(60) Provisional application No. 60/536,143, filed on Jan. 13, 2004.

(51) Int. Cl.
*A61K 31/34* (2006.01)
*A61K 31/355* (2006.01)
*A61K 31/19* (2006.01)
*A61K 31/07* (2006.01)

(52) U.S. Cl. ............... 514/474; 514/458; 514/570; 514/571; 514/725

(58) Field of Classification Search .............. None
See application file for complete search history.

(56) References Cited

U.S. PATENT DOCUMENTS

| | | | |
|---|---|---|---|
| 2,132,662 A | 10/1938 | Volwiler et al. |
| 2,134,246 A | 10/1938 | Basel et al. |
| 2,140,989 A | 12/1938 | Eisenbrand et al. |
| 2,150,140 A | 3/1939 | Wamat |
| 2,161,651 A | 6/1939 | Roberts |
| 2,165,184 A | 7/1939 | Pastemack et al. |
| 2,187,467 A | 1/1940 | Stuart |
| 2,249,903 A | 7/1941 | Lautenschlager et al. |
| 2,294,937 A | 9/1942 | Ruskin |
| 2,297,212 A | 9/1942 | Gockel |
| 2,400,171 A | 5/1946 | Ruskin |
| 2,442,461 A | 6/1948 | Karrer et al. |
| 2,585,580 A | 2/1952 | Opplt |
| 2,721,161 A | 10/1955 | Maiese |
| 4,199,469 A | 4/1980 | Walzer |
| 4,294,852 A | 10/1981 | Wildnauer et al. |
| 4,367,157 A | 1/1983 | Sherman |
| 4,372,874 A | 2/1983 | Modrovich |
| 4,722,936 A | 2/1988 | Jacob |
| 4,818,521 A | 4/1989 | Tamabuchi |
| 4,847,071 A | 7/1989 | Bissett et al. |
| 4,938,969 A | 7/1990 | Schinitsky et al. |
| 4,946,671 A | 8/1990 | Bissett et al. |
| 4,954,332 A | 9/1990 | Bissett et al. |
| 4,983,382 A | 1/1991 | Wilmott et al. |
| 5,023,235 A | 6/1991 | N'Guyen et al. |
| 5,140,043 A | 8/1992 | Darr et al. |
| 5,536,500 A | 7/1996 | Galey et al. |
| 5,703,122 A | 12/1997 | Duffy |
| 5,736,567 A | 4/1998 | Cantin et al. |
| 6,146,664 A | 11/2000 | Siddiqui |
| 6,346,254 B1 | 2/2002 | Streicher et al. |
| 6,521,271 B1 | 2/2003 | Phan |
| 6,524,599 B2 | 2/2003 | Pinnell |
| 2002/0034548 A1 | 3/2002 | Parr et al. |
| 2003/0152536 A1 | 8/2003 | Pauly et al. |
| 2003/0152656 A1 | 8/2003 | Pinnell et al. |
| 2004/0152912 A1 | 8/2004 | Taniguchi et al. |

FOREIGN PATENT DOCUMENTS

| | | |
|---|---|---|
| EP | 0664290 A1 | 7/1995 |
| EP | 1 121 926 | 8/2001 |
| FR | 2655054 | 5/1991 |
| JP | 59 015477 | 1/1984 |
| JP | S63-37087 | 8/1989 |
| JP | 6009603 | 1/1994 |
| WO | WO 00/76492 | 12/2000 |
| WO | WO 00/78283 | 12/2000 |
| WO | WO 01/91715 | 12/2001 |
| WO | WO 02/019972 | 3/2002 |
| WO | WO 02/081027 | 10/2002 |

OTHER PUBLICATIONS

International Search Report in a counterpart PCT Application No. PCT/US2005/001053, mailed May 11, 2005 and Notice of Mailing regarding same.

Written Opinion of the International Searching Authority in a counterpart PCT Application No. PCT/US2005/001053, mailed May 11, 2005.

Chemical Abstracts, "110:198950r Cosmetic skin lightening and UV-absorbing compositions containing isoferulic acid (salts), ascorbic acid (derivatives), and polyalcohols", Shiyaku, et al., vol. 110, (1989), (Pub. Nov. 1988).

Bissett, et al., "Photoprotective effect of superoxide-scavenging antioxidants against ultraviolet radiation-induced chronic skin damage in the hairless mouse", pp. 58-60, Photodermatol Photoimmunol Photomed 1990: 7: pp. 58 and 60.

(Continued)

*Primary Examiner*—Raymond J. Henley, III
(74) *Attorney, Agent, or Firm*—Randall C. Brown; Haynes and Boone, LLP

(57) ABSTRACT

The present invention relates to ascorbic acid single-phase solution compositions that provide enhanced stability, enhanced solubility and an enhanced photoprotective effect as compared to prior compositions. The compositions comprise L-ascorbic acid; a cinnamic acid derivative such as p-coumaric acid, ferulic acid, caffeic acid, sinapinic acid, a derivative thereof, and a combination thereof; a solvent comprising a glycol ether and an alkanediol; and water; the composition having a pH of no more than about 3.5. The compositions may also comprise a form of Vitamin E and are useful for treatment of radical-induced damage to a subject, particularly the skin of a subject.

42 Claims, 6 Drawing Sheets

OTHER PUBLICATIONS

Brand, et al., "Going with the grain. (Ingredients: Rice)", Soap Perfumery & Cosmetics, 76, 3, 40(4), ISSN: 0037-749X, pp. 1-6, (1993), Mar. 2003.

Buettner, et al., "Catalytic Metals, Ascorbate and Free Radicals; Combinations to Avoid" Radiation Res. 145, 532-541 (1996), Presented at the Fenton Centennial Symposium at the 42nd Annual Meeting of the Radiation Research Society, San Jose CA, Apr. 1995.

Buettner & Schafer 3, "AscH$_2$ is a Di-acid", Ascorbate Chemistry, Oxygen Society Education Program, (Date Unknown.).

Buettner & Schafer 4, "Forms of Ascorbate", Ascorbate Chemistry, Oxygen Society Education Program, (Date Unknown.).

Buettner & Schafer 5, "Ascorbate Falling Apart", Ascorbate Chemistry, Oxygen Society Education Program,(Date Unknown.).

Buettner & Schafer 6, "Kinetics of AscH- Reactions", Ascorbate Chemistry, Oxygen Society Education Program,(Date Unknown.).

Buettner & Schafer 15, "The Pecking Order", Ascorbate Chemistry, Oxygen Society Education Program, (Date Unknown.).

Ciminera, et al., "Stable Ascorbic Acid Solution for Parental Use" Scientific Edition, Journal Of The American Pharmaceutical Association, pp. 363-365, 1946.

Cosmetics & Personal Care Market, Eastman referencing J. Am. Coll. Toxicol., 4(5), 1985.

Deutsch, "Review Dehydroascorbic Acid" Journal of Chromatography A 881 (2000) pp. 299-307, © 2000 Elsevier Science B.V.

Diethylenglykolmonoethylether, pp. 1-2, Apr. 13, 2003 © ab 1999 Ralf Rebmann http://www.gifte.de/diethylenglykolmonoethylether.htm.

Diethylene Glycol Monoethyl Ether, H&S: Diethylene Glycol Monoethyl Ether, NTP Chemical Repository, Last Revised Aug. 13, 2001, pp. 1-8, http://ntp-dp.niehs.nih.gov/NTP_Reports/NTP_Chem_HS_HTML/NTP_Chem1/Radian111 . . .

Englard et al., "The Biochemical Functions of Ascorbic Acid", Annual Reviews Inc., 1986, pp. 365-395, 398-406.

Fox, "Topical bioactive materials (part 2)" Cosmetics and Toiletries, Sep. 1994, pp. 83 (22), v109, n9, ISSN: 0361-4387.

"HORT640—Metabolic Plant Physiology", Ligin biosynthesis—Secondary products derived from aromatic amino acids, Aug. 20, 2003, pp. 1-3, http://www.hort.purdue.edu/rhodev/hort640c/secprod/se00016.htm.

Imai, et al., "The Antiscorbutic Activity of L-Ascorbic Acid Phosphate Given Orally and Percutaneously in Guinea Pigs", The Japanese Journal of Pharmacology, vol. 17, No. 2, Jun. 1967, pp. 317-324.

Increasing use of high sun protection factors in sunscreen products, printed Sep. 15, 2003, 2 pages http://www.roche.com/pages/facets/1/uvfilte.htm.

Kunert et al., "The Effect of Vitamin C on in vivo Lipid Peroxidation in Guinea Pigs as Measured by Pentane and Ethane Production", LIPIDS, vol. 18, No. 4, (1983), pp. 271-274.

Lewin, "Vitamin C: Its Molecular Biology and Medical Potential", Academic Press, 1976, pp. 4-63, 196-223.

Lin, "UV photoprotection by combination topical antioxidants vitamin C vitamin E" © 2003 American Academy of Dermatology, Inc., J Am Acad Dermatol, pp. 866-874, vol. 48, No. 6.

Lu, "Interactions of lipoic acid radical cations with vitamins C and E analogue and hydroxycinnamic acid derivatives" Archives of Biochemistry and Biophysics 406, © 2002 Elsevier Science (USA), pp. 78-84, Academic Press.

Merck & Co., Inc. "Ascorbic Acid Vitamin C in Wound Healing", Annotated Bibliography, pp. 1-15, Merck Service Bulletin, Mar. 1941.

Meucci et al., "Ascorbic Acid Stability in Aqueous Solutions", Acta Vitaminol. Enzymol., 1985, 7(3-4) pp. 147-154.

Pinnell, "Cutaneous photodamage, oxidative stress, and topical antioxidant protection" Continuing Medical Education, From Duke University Medical Center, © 2003 by the American Academy of Dermatology, Inc., pp. 1-22, J Am Acad Dermatol, vol. 48, No. 1.

Pinnell, "Topical L-Ascorbic Acid: Percutaneous Absorption Studies" Dermatol. Surg. 2001; 27:137-142 © Feb. 2001 by the American Society for Dermatologic Surgery, Inc., pp. 137-142, published by Blackwell Science, Inc., ISSN: 1076-0512/01.

Propanediol by HyperDictionary.com, © 2000-2003 Webnox Corp.

Propylene glycol, The Chemistry Store.com, http://www.chemistrystore.com/propylene_glycol.htm, 2002.

Rice-Evans, "Structure-Antioxidant Activity Relationships of Flavonoids and Phenolic Acids" Review Article, Free Radical Biology & Medicine, pp. 933, 948-953, vol. 20, No. 7, © 1996 Elsevier Science, Inc.

Safety (MSDS) data for 1,2-propanediol, pp. 1-2, Updated Sep. 4, 2003, http://ptcl.chem..ox.ac.uk/MSDS/PR/1,2-propanedio.html.

Saija, "In vitro and in vivo evaluation of caffeic and ferulic acids as topical photoprotective agents", International Journal of Pharmaceutics, pp. 39-47 © 2000, Elsevier Science B.V.

Schaefer et al., "pH Dependence", pp. 739-740, Skin Permeability, Springer-Verlang Berlin Heidelberg New York 1982.

Takashima, et al., "Ascorbic Acid Esters and Skin Pigmentation", American Perfumer and Cosmetics, vol. 86, No. 7, Jul. 1971, pp. 29-36.

Transcutol® P and Transcutol® HP, printed Sep. 19, 2003, http://www.gattefosse.com/pharma/products/transcup.htm.

Vitamin-C Science, printed Sep. 15, 2003, http://www.skinceuticals.com/science/vaminc.html.

STABILIZED ASCORBIC ACID COMPOSITIONS AND METHODS THEREFOR

This application claims the benefit of U.S. Provisional Patent Application No. 60/536,143, filed Jan. 13, 2004, which is incorporated by reference in its entirety.

FIELD OF THE INVENTION

The present invention relates to the field of stabilized ascorbic acid cosmetic and dermatological compositions for treatment of skin to address radical-induced damage.

BACKGROUND OF THE INVENTION

Aging skin is the result of more than just chronological age. Skin is exposed to environmental elements that cause radicals to form in the skin. These radicals attack the collagen layer of the skin and break it down, causing lines and wrinkles to appear. This process is commonly called photo-aging. Diseases and disorders of skin that also may result from radical damage include skin cancer, skin irritation or inflammation, dermatitis, allergy, psoriasis, acne, eczema, rosacea, and radiation exposure.

Application of antioxidants can help prevent radical-induced damage in skin. Applying Vitamin C, for example, to the skin can provide antioxidant protection, prevent photo-aging, and stimulate collagen production. However, not all Vitamin C formulations produce these benefits due to lack of stability.

Numerous approaches to achieving a stable formulation of ascorbic acid include micronization (PCT publication No. WO 02/019972 to Vivier, G.), low pH (U.S. Pat. No. 5,140,043 to Darr, D. and Pinnell, S.), formation of suspensions or dispersions, lowered water activity, addition of various carriers, and derivatization, in particular, esterification. Regardless of the approach, these methods generally are inadequate to prevent degradation of ascorbic acid for long term storage, for example, for a period of one year at room temperature. Derivatization, while assisting in preventing degradation, for example, also may cause a decreased activity.

The challenge of achieving stability while maintaining activity of ascorbic acid compositions is addressed by the present inventors.

SUMMARY OF THE INVENTION

The present invention relates to single-phase solution compositions of L-ascorbic acid that provide enhanced stability, enhanced solubility and an enhanced photoprotective effect as compared to prior compositions. The single-phase solution compositions comprise by weight 5% to 40% L-ascorbic acid; 0.2% to 5.0% of a cinnamic acid derivative, such as p-coumaric acid, ferulic acid, caffeic acid, sinapinic acid, a derivative thereof, or a combination thereof; 10% to 60% of a solvent comprising a glycol ether and an alkanediol; and water; the composition having a pH of no more than about 3.5. When the cinnamic acid derivative is present at an amount greater than 0.5%, the composition further comprises a surfactant in an amount of 1.5% to 5.0%.

The single-phase solution compositions may also comprise a form of Vitamin E and a surfactant, or a form of Vitamin A and a surfactant.

In one embodiment of the invention, an ascorbic acid single-phase solution composition comprises by weight, 5% to 20% L-ascorbic acid; 0.5% to 5.0% of a cinnamic acid derivative such as p-coumaric acid, ferulic acid, caffeic acid, sinapinic acid, a derivative thereof, or a combination thereof; 10% to 60% of a solvent comprising a glycol ether and an alkanediol; 0.5% to 1.5% of a preservative such as phenoxyethanol; 0.3% to 1.5% of a moisturizer such as panthenol; 0.5% to 5.0% of a base such as triethanolamine; 0.05% to 0.3% of a viscosity enhancer such as sodium hyaluronate; and water to 100%, the composition having a pH of no more than about 3.5. When the cinnamic acid derivative is present at an amount of greater than 0.5%, the composition further comprises a surfactant in an amount of 1.5% to 5.0%.

A further embodiment of the invention is a process for stabilizing ascorbic acid for storage, the process comprising combining 0.2% to 0.5% of a cinnamic acid derivative, such as p-coumaric acid, ferulic acid, caffeic acid, sinapinic acid, a derivative thereof, or a combination thereof; 10% to 60% of a solvent comprising a glycol ether and an alkanediol; and water; and adding 5% to 40% L-ascorbic acid to form a clear single-phase solution composition of stabilized ascorbic acid, the composition having a pH of no more than about 3.5.

A further process for stabilizing L-ascorbic acid for storage comprises combining water and 0.5% to 5.0% of a cinnamic acid derivative selected from the group consisting of p-coumaric acid, ferulic acid, caffeic acid, sinapinic acid, a derivative thereof, or a combination thereof to form a first solution. Separately, 10% to 60% of a solvent comprising a glycol ether and an alkanediol, and 1.5% to 5.0% surfactant are combined to form a second solution. The first solution and the second solution are mixed to form a mixed solution. L-ascorbic acid at 5% to 40% is added to the mixed solution and the solution stirred to form a single-phase clear solution composition of stabilized ascorbic acid, the composition having a pH of no more than about 3.5.

Another embodiment of the invention is a method of treating a subject for effects of radical-induced damage, comprising administering to the subject a stabilized single-phase solution composition comprising by weight, 5% to 40% L-ascorbic acid; 0.2% to 5.0% of a cinnamic acid derivative such as p-coumaric acid, ferulic acid, caffeic acid, sinapinic acid, a derivative thereof, or a combination thereof; 10% to 60% of a solvent comprising a glycol ether and an alkanediol; and water; the composition having a pH of no more than about 3.5. When the cinnamic acid derivative is present at an amount greater than 0.5%, the composition further comprises a surfactant in an amount of 1.5% to 5.0%. The method of treating includes prophylactic and therapeutic treatment, i.e., preventing damage, retarding damage, or treating damage, or preventing, retarding or treating symptoms of damage. The composition used in the method may further comprise a form of Vitamin E and a surfactant, or a form of Vitamin A and a surfactant.

A further embodiment of the invention is a method of treating the skin of a subject for effects of radical-induced damage, comprising administering to the skin of the subject a stabilized single-phase solution composition comprising by weight, 5% to 20% L-ascorbic acid; 0.5% to 5.0% of a cinnamic acid derivative such as p-coumaric acid, ferulic acid, caffeic acid, sinapinic acid, a derivative thereof, or a combination thereof; 10% to 60% of a solvent comprising a glycol ether and an alkanediol; 0.5% to 1.5% phenoxyethanol; 0.3% to 1.5% panthenol; 0.5% to 5.0% triethanolamine; 0.05% to 0.3% sodium hyaluronate; 0.3% to 2.0% of a form of Vitamin E; 1.5% to 5.0% of a surfactant; and water to 100%, the composition having a pH of no more than about 3.5. The composition may further comprise a Vitamin A derivative.

A further embodiment of the present invention is a method of treating the skin of a subject for effects of radical-induced damage, comprising administering to the skin of the subject a stabilized single-phase solution composition comprising by weight, 5% to 40% L-ascorbic acid; 0.5% to 5.0% of a cinnamic acid selected from the group consisting of p-coumaric acid, ferulic acid, caffeic acid, sinapinic acid, a derivative thereof, and a combination thereof; 10% to 60% of a solvent comprising a glycol ether and an alkanediol; 0.5% to 1.5% phenoxyethanol; 0.3% to 1.5% panthenol; 0.5% to 5.0% triethanolamine; 0.05% to 0.3% sodium hyaluronate; 0.3% to 2.0% of a form of Vitamin E; 1.5% to 5.0% of a surfactant; 0.3% to 2.0% retinol; and water to 100%, the composition having a pH of no more than about 3.5. As in the embodiment above, the method of treating the skin includes preventing damage, retarding damage, or treating damage to the skin, or preventing, retarding or treating symptoms of damage to the skin.

▨ control, untreated skin;
▩ composition A of Table 4;
≡ composition B of Table 4;
■ composition C of Table 4;
▦ composition E of Table 4.

Figure 1:
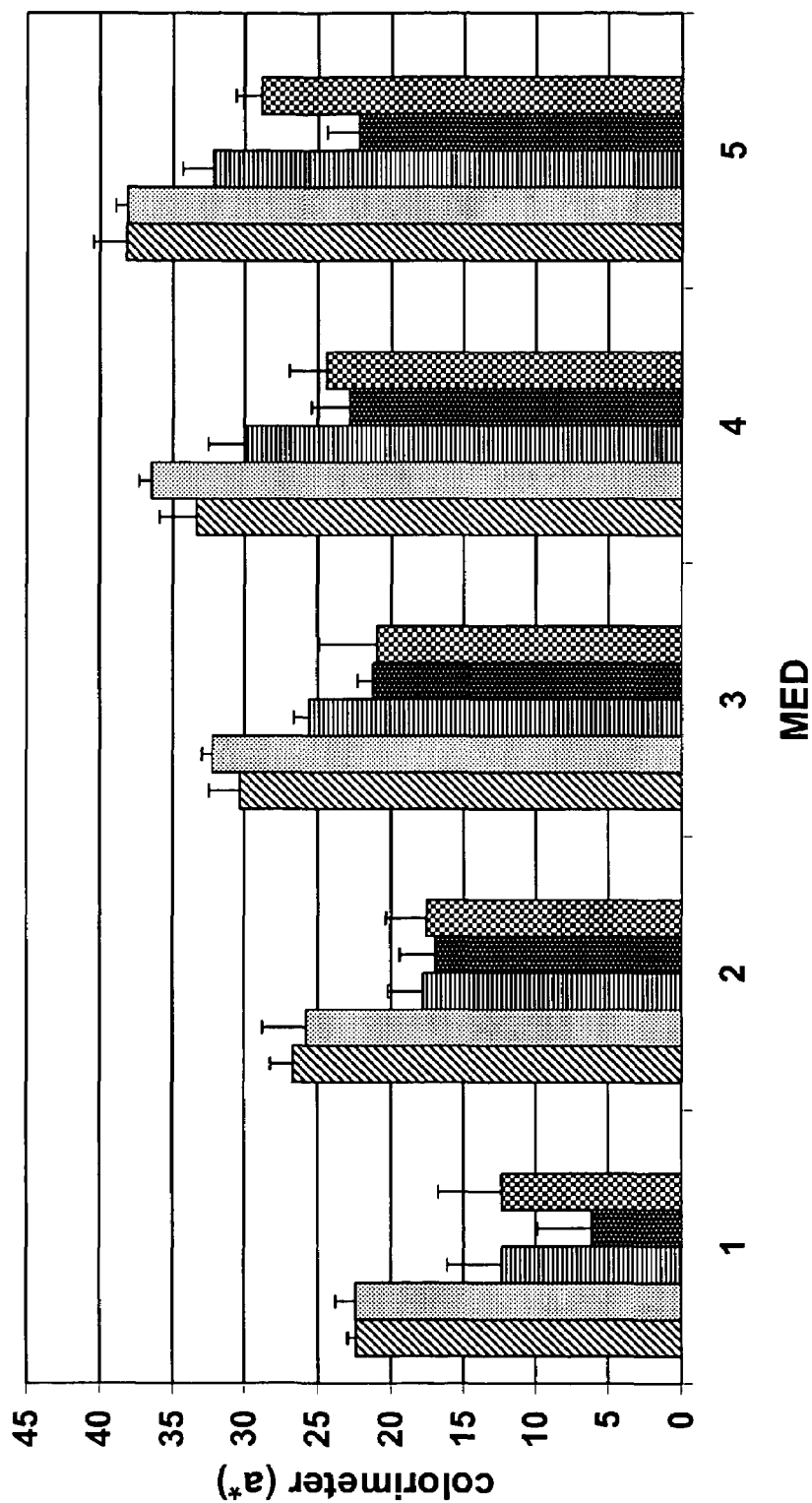
FIG. 1. Stabilized single-phase solution compositions or control compositions were applied to pig skin daily for four days. Skin was irradiated with solar-simulated UV irradiation as described in Example 4. Colorimeter readings for 1× to 5× Minimal Erythemal Dose (MED) were made the next day. Symbols are as follows.
Figure 2:

FIG. 2. Stabilized single-phase solution compositions were applied to pig skin as for FIG. 1. Colorimeter readings for 2× to 10× MED were made the next day. Symbols are as follows:

▥ composition D of Table 4;
≡ composition F of Table 4.

Figure 3:
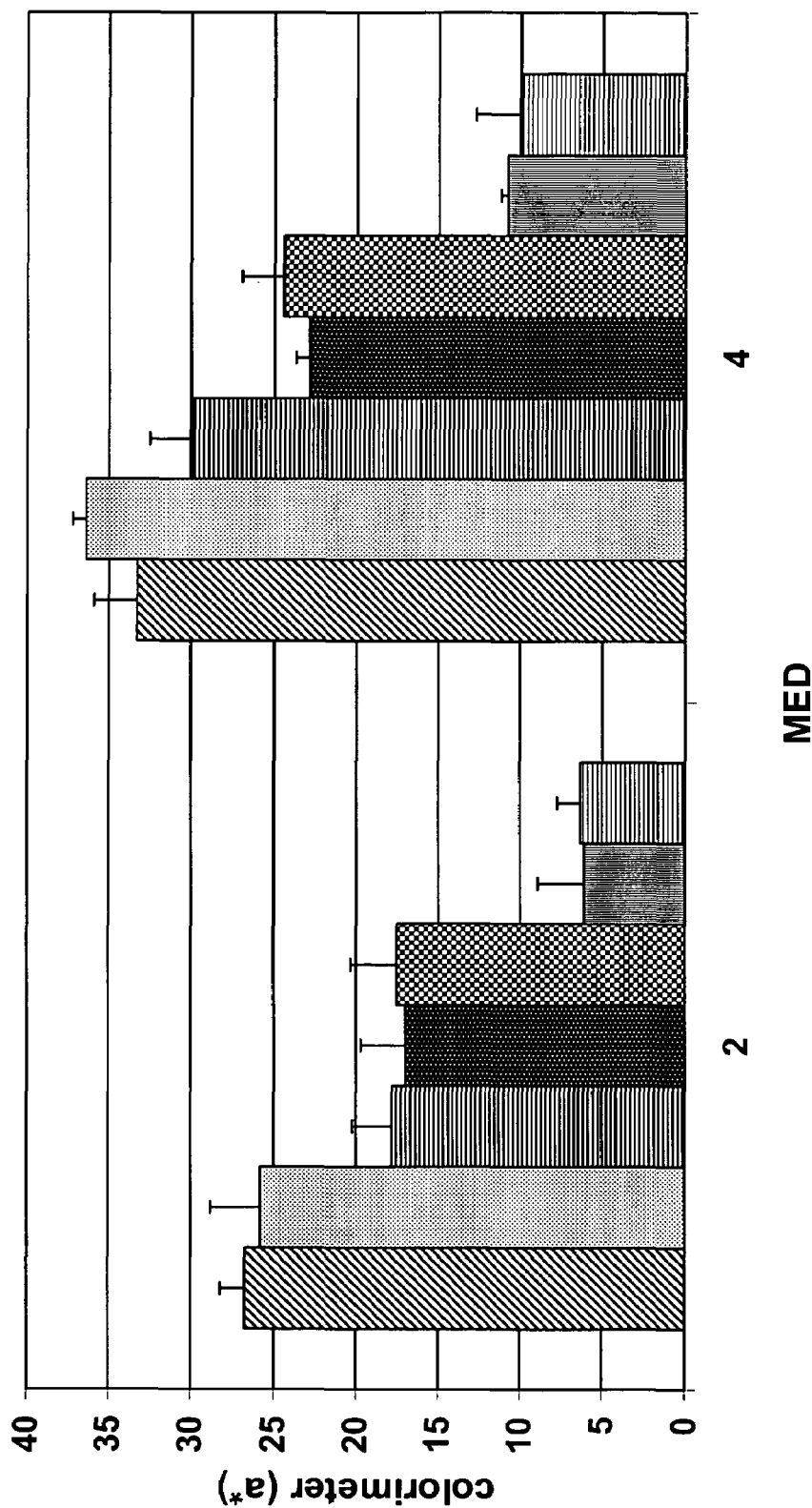

FIG. 3. Data from FIG. 1 and FIG. 2 are plotted together for 2× and 4×MED results for comparison. Symbols are as in FIG. 1 and FIG. 2.

Figure 4:
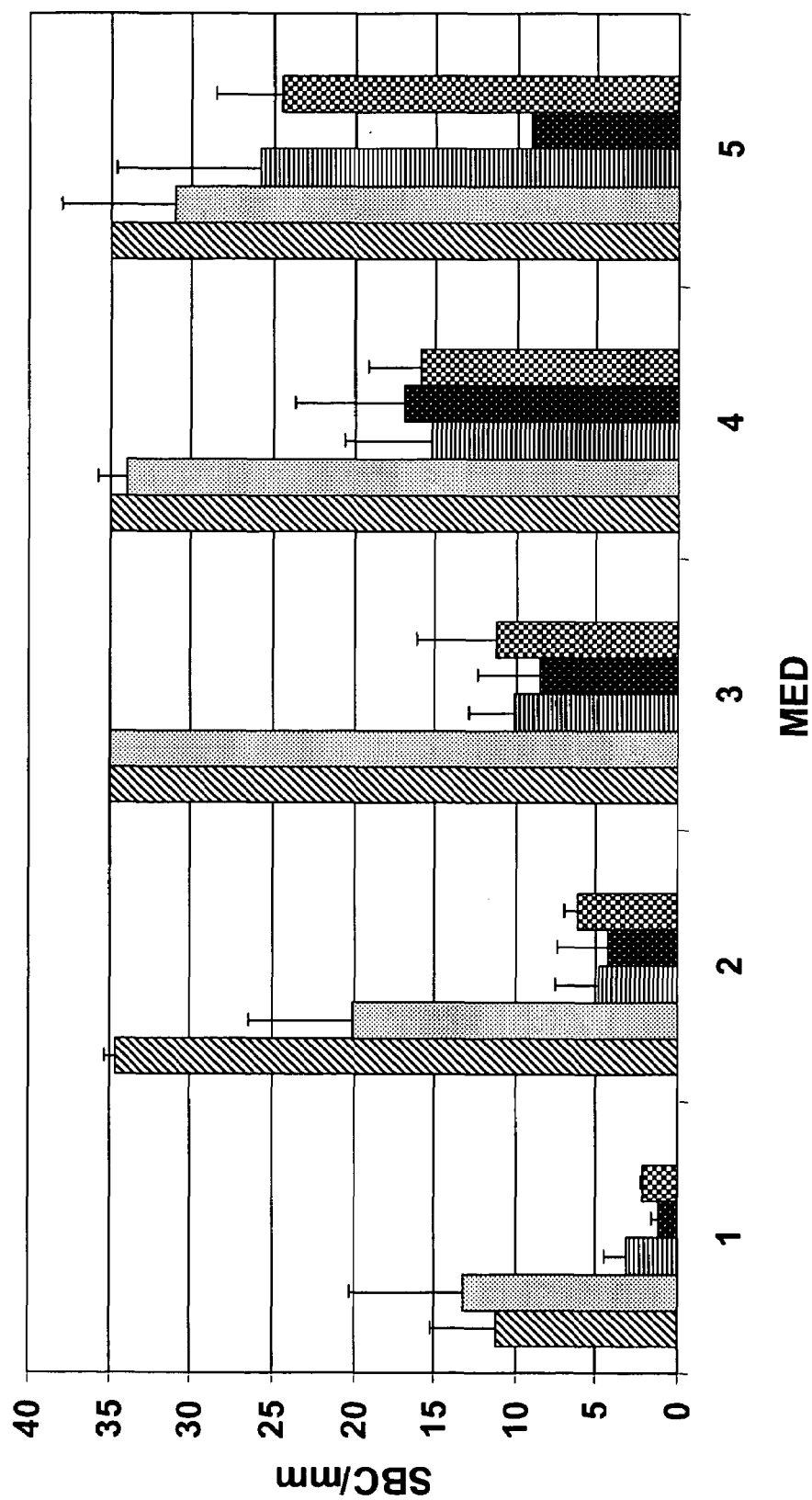

FIG. 4. Stabilized single-phase solution compositions or control compositions were applied to pig skin daily for four days. Skin was irradiated with solar-simulated UV irradiation and biopsy specimens were stained and analyzed for sunburn cells/mm as described in Example 4. The data are for 1× to 5× MED. Symbols are as follows:

▨ control, untreated skin;
▩ composition A of Table 4;
≡ composition B of Table 4;
■ composition C of Table 4;
▦ composition E of Table 4.

Figure 5:

FIG. 5. Stabilized single-phase solution compositions were applied to pig skin daily as for FIG. 4. The data are for 2× to 10× MED. Symbols are as follows:

▥ composition D of Table 4;
≡ composition F of Table 4.

Figure 6:

FIG. 6. Data from FIG. 4 and FIG. 5 are plotted together for 2× and 4× MED results for comparison. Symbols are as in FIG. 4 and FIG. 5.

DETAILED DESCRIPTION OF THE INVENTION

Ascorbic acid in aqueous solutions is readily degraded into oxidized forms that subsequently become a source of free radicals. The oxidation reactions consume ascorbic acid and reflect on the stability of ascorbic acid. In the present studies, cinnamic acid derivatives were tested for their effect on the stability of ascorbic acid. In addition, the effect of the presence of solvents and that of solvent concentration were studied. The photoprotective effect of stabilized formulations is also provided.

The single-phase solution compositions of ascorbic acid of the present invention include L-ascorbic acid, a cinnamic acid derivative, such as p-coumaric acid, ferulic acid, caffeic acid, sinapinic acid, a derivative thereof, and a combination thereof, a solvent comprising a glycol ether and an alkanediol, water, and optionally, phenoxyethanol, panthenol, triethanolamine, and sodium hyaluronate. Single-phase solution compositions having 0.5% or greater of the cinnamic acid derivative also comprise a surfactant. The composition may also include a form of Vitamin E and a surfactant, and/or a form of Vitamin A and a surfactant. The composition has a pH of no more than about 3.5 or about 2.5 to 3.0.

Compositions of the present invention are single-phase solution compositions. "Single-phase solution compositions" means herein that the composition has one phase, that of a liquid phase, is homogenous, and has essentially no particulate material, microparticles, or emulsified particles present in the composition.

L-ascorbic acid: L-ascorbic acid is commercially available from Sigma-Aldrich (St. Louis, MO.), for example. In one embodiment, the L-ascorbic acid is purchased at 99% purity. Compositions provided herein contain L-ascorbic acid in an amount of 5% to 40% by weight. By "5% to 40% by weight" is meant herein to include the 5% and 40% amounts. In one embodiment of the composition, the amount of L-ascorbic acid is 10% to 35% and, in another embodiment, the amount of ascorbic acid is 10% to 30%. In further embodiments, the amount of ascorbic acid is 10% to 25%, 10% to 20%, or 15% to 20%. The required pH of the composition ensures that greater than 82% of the ascorbic acid remains in a protonated, uncharged form as disclosed in U.S. Pat. No. 5,140,043, Aug. 18, 1992, the entire disclosure of which is incorporated by reference herein. The ascorbic acid may be provided by the addition of any reducing analog of ascorbic acid, such as D-isoascorbic acid or by the addition of other small reducing compounds such as, but not limited to, glutathione, L-cysteamine, and the like. Such forms would be expected to provide an equivalent composition to that claimed and are within the scope of the invention.

Cinnamic Acid Derivatives: Cinnamic acid derivatives that improve the stability of ascorbic acid are contemplated to be included in the compositions of the present invention.

Cinnamic acid derivatives contemplated herein include ferulic acid, caffeic acid, p-coumaric acid, sinapinic acid, combinations thereof, cis and trans isomers thereof, salts thereof, and equivalent derivatives thereof. Equivalent derivatives thereof include those cinnamic acid derivatives having substitutions on the hydroxyl groups of the aromatic ring such as short chain aliphatic groups (one to six carbon atoms) or long chain aliphatic groups (seven to twenty-four carbon atoms) to form an ether, or such aliphatic groups substituted with alkyl, alkoxy, hydroxyl, amino, or amido, for example, to form a substituted ether. Equivalent derivatives thereof further include those cinnamic acid derivatives having modifications of the methoxy group(s) of the aromatic ring to short chain aliphatic groups (two to six carbon atoms) or to long chain aliphatic groups (seven to twenty-four carbon atoms) to form a longer chain ether, or such aliphatic groups substituted with alkyl, alkoxy, hydroxyl, amino, or amido, for example, to form a substituted long chain ether. The 3-carboxy group of a cinnamic acid derivative may also be converted to esters or amides having aliphatic groups of up to 24 carbons or an aromatic group, for example. Cis and trans isomers of the cinnamic acid derivatives are included herein since the cis isomer is readily converted to the trans isomer. Salts of the cinnamic acid derivatives are included herein. In one embodiment, the cinnamic acid derivative is a triethanolamine salt.

Cinnamic acid derivatives are present in the compositions of the present invention in an amount of 0.2%, 0.5%, 1.0%, 1.5%, 2.0%. 2.5%, 3.0%, 4.0% or up to 5.0% by weight of the composition, or amounts within the range of 0.2% to 5.0%. Caffeic acid, also known as 3-(3,4-dihydroxyphenyl)-2-propenoic acid, is found in many fruits, vegetables, seasonings and beverages consumed by humans. Caffeic acid is present in such goods in conjugated forms such as chlorogenic acid. Para-coumaric acid, also known as 3-(4-hydroxyphenyl)-2-propenoic acid or p-hydroxycinnamic acid, is found in various plants, including lignin forming plants. Trans-ferulic acid, also known as 3-(4-hydroxy-3-methoxyphenyl)-2-propenoic acid or 4-hydroxy-3-methoxycinnamic acid, is also widely distributed in small amounts in plants. Sinapinic acid, also known as 3,5-dimethoxy4-hydroxycinnamic acid, is from black mustard seeds. Caffeic acid, para-coumaric acid, trans-ferulic acid and sinapinic acid are commercially available from Sigma-Aldrich.

Solvent comprising a Glycol Ether and an Alkanediol: In one embodiment, the glycol ether is di(ethylene glycol) ethyl ether, also known as ethoxy diglycol, 2-(2-ethoxyethoxy)ethanol, diglycolmonoethyl ether, ethyl diethylene glycol, ethylene diglycol monoethyl ether, CARBITOL®, or TRANSCUTOL®, for example. Di(ethylene glycol) ethyl ether is commercially available from Sigma-Aldrich. Further glycol ethers include methoxyisopropanol, PPG-2 methyl ether, PPG-3 methyl ether, propylene glycol butyl ether, PPG-2 butyl ether, phenoxyisopropanol, butoxyethanol, butoxydiglycol, methoxydiglycol, phenoxyethanol, PPG-3 butyl ether, PPG-2 propyl ether, propylene glycol propyl ether, or dipropylene glycol dimethyl ether, for example, from the Dow Chemical Company, Midland, Mich.

The alkanediol is propanediol, also known as propylene glycol, in particular, 1,2-propanediol. The alkanediol is commercially available from Sigma-Aldrich. The alkanediol may be 1,3-butanediol, 1,2-butanediol, or 1,2-ethanediol, for example.

The solvent comprises 10% to 60% by weight of the composition. In one embodiment, the solvent comprises 15%, 20%, 25%, 30%, 35%, 40%, 45%, 50%, or 55% of the composition. The ratio of glycol ether to alkanediol is about 1.5:1, 2:1, 3:1 and up to about 4:1. In particular, the ratio of glycol ether to alkanediol is about 2:1.

Preservatives: Preservatives having antibacterial activity are optionally present in the compositions of the present invention. Any preservative commonly used in cosmetic formulations is an acceptable preservative for the compositions herein, such as phenoxyethanol, members from the paraben family such as the methyl, ethyl, propyl, butyl or isobutyl parabens, 4-hydroxy benzoic acid, benzoic acid, sorbic acid, dehydroacetic acid, triclosan, benzyl alcohol, chlorophenesin, or salicylic acid, for example. Phenoxyethanol is commercially available from Sigma-Aldrich. At more concentrated amounts of solvent, members from the paraben family may be used as a preservative.

Moisturizers: Moisturizers are optionally present in the compositions of the present invention. Any moisturizer commonly used in cosmetic formulations is an acceptable moisturizer for the compositions herein, such as Panthenol (pro-Vitamin B5), commercially available from Sigma-Aldrich. Panthenol has additional desirable biological properties, such as wound healing properties.

Base: A base for forming a salt of a cinnamic acid is desired herein where the acid is not already in a salt form. A base may be an organic base such as triethanolamine, aminomethylpropanol, diisopropanolamine, triisopropanolamine, or an inorganic base such as sodium hydroxide, potassium hydroxide, or ammonium hydroxide, for example. An inorganic salt of the cinnamic acid is acceptable if the concentration of the cinnamic acid is low such that the solution remains clear. Bases, such as triethanolamine, for example, are commercially available from Sigma-Aldrich.

Viscosity Enhancer: A viscosity enhancer is optionally present in the compositions of the present invention. Any viscosity enhancer commonly used in cosmetics is acceptable for compositions herein. Sodium hyaluronate is an example of a viscosity enhancer that also provides a slip effect that improves the feeling of the composition on the skin. Sodium hyaluronate also assists in keeping moisture on the skin and improves absorption of the composition. Carboxymethylcellulose, for example, is another viscosity enhancer commonly used in cosmetics.

Water: Water to complete 100% by weight of the composition is distilled or deionized, but any water may be used that does not contain contaminants that would affect the stability of the ascorbic acid composition.

Surfactant: Presence of a surfactant is needed in compositions of the present invention when the composition contains a form of Vitamin E, or other hydrophobic agent, or concentrations of a cinnamic acid derivative at greater than 0.5% by weight, for example, to facilitate solubilization. A surfactant may be a nonionic surfactant such as polyoxyethylene sorbitan monolaureate (TWEEN®), (i.e., TWEEN®20), polyoxyethylene 23 lauryl ether (BRIJ®–35) or polyoxyethylated octyl phenol (TRITON®); a zwitterionic surfactant such as 3-((3-cholamidopropyl) dimethylammonio)-1-propane sulfonate (CHAPS®); a cationic surfactant; or an anionic surfactant such as cholate, deoxycholate, sodium dodecylsulfate, or TWEEN®–80. The surfactant may be present in an amount of 1.5%, 2.0%, 2.5%, 3.0%, 3.5%, 4.0%, 4.5%, or 5.0% by weight of the composition.

Form of Vitamin E: By "a form of Vitamin E" is meant herein a form of tocopherol selected from alpha, beta, delta, and gamma tocopherols, and alpha, beta, delta and gamma tocotrienols, and combinations or derivatives thereof. In one embodiment, the form of Vitamin E is an alpha, beta, delta, or gamma tocopherol and, in another embodiment, the form of Vitamin E is an alpha tocopherol. Salts or derivatives of tocopherols include pharmaceutically acceptable compounds such as acetate, sulfate, succinate, nicotinate, palmitate, allophanate, phosphate, quinone, or halogenated derivatives, esters, or stereoisomers, for example. The invention encompasses the use of Vitamin E derivatives in which substitutions, additions, and other alterations have been made in the 6-chromanol ring and/or side chain, with the proviso that the derivatives maintain the antioxidant activity of Vitamin E. Additional tocopherols can be constructed by conjugation to the ring structure or side chain of various other moieties, such as those containing oxygen, nitrogen, sulfur and/or phosphorus. Tocopherol derivatives can also be made by modifying the length of the side chain from that found in tocopherols such as alpha-, beta-, delta- and gamma-tocopherol. Tocopherols can also vary in stereochemistry and saturation of bonds in the ring structure and side chain.

Additional tocopherol derivatives, including prodrugs, can be made by conjugation of sugars or other moieties to the side chain or ring structure. Tocopherols include without limitation stereoisomers (e.g., + and − stereoisomers of alpha-tocopherol; (+/−) indicates a racemic mixture) or mixtures of structurally distinct tocopherols (e.g., alpha–plus gamma-tocopherol). Tocopherols may be obtained from Roche, Nutley, N.J., for example.

Further optional ingredients: Further optional ingredients include, for example, cosmetic or dermatological ingredients known to one of skill in the art, including further antioxidants such as Vitamin A derivatives such as a retinoid, retinol, retinal, retinoic acid, a retinoic acid salt, a derivative or analog thereof, or a mixture thereof, lipoic acid, seleno-L-methionine, or flavonoids that lack undesirable color. The compositions may also contain mild surfactants, oil components, emulsifiers, pearlizing waxes, consistency factors, thickeners, superfatting agents, stabilizers, polymers, silicone compounds, fats, waxes, lecithins, phospholipids, biogenic agents, further UV protection factors, deodorants, antiperspirants, antidandruff agents, film formers, swelling agents, insect repellents, self-tanning agents, hydrotropes, solubilizers, preservatives, perfume oils, or dyes, for example as further additives.

Preparations: The compositions of the present invention may be used for the production of cosmetic preparations, or dermatological preparations, more particularly topical treatment preparations, that may be formulated as single-phase solution compositions, cosmetic serums, or aerosols, for example. Topical application to a surface may be a surface such as the mucus membrane or the skin, for example.

Process of Making Stabilized Ascorbic Acid Compositions having less than 0.5% by Weight Cinnamic Acid Derivative: Compositions of ascorbic acid are made using the following procedures: water, solvents, phenoxyethanol, panthenol, triethanolamine, and the cinnamic acid derivative are stirred together until dissolved to a clear solution. Sodium hyaluronate is sprinkled on the surface of the solution without stirring and the mixture allowed to form a gel without stirring for about 3 hours. After the three hour period, the gel is stirred to obtain a uniform viscous solution. The solution is degassed under vacuum and saturated with an inert gas such as argon or nitrogen. This degassing and saturating procedure was carried out three times. Ascorbic acid is added with stirring, the solution is again degassed under vacuum and saturated with an inert gas, and then stirred for 30 to 45 minutes to yield a clear solution which is then degassed and saturated with an inert gas.

Process of Making Stabilized Ascorbic Acid Compositions having a Cinnamic Acid Derivative at 0.5% or Greater by Weight or having a Hydrophobic Component: Compositions having increased concentrations of cinnamic acid derivative or a hydrophobic component such as tocopherol or retinol are made by mixing water, triethanolamine, cinnamic acid derivative, and panthenol until a clear solution is formed. Sodium hyaluronate is sprinkled on the surface of the solution and allowed to dissolve for about three hours to form a first solution. Separately, a mixture of solvents, surfactant, phenoxyethanol, and hydrophobic component is gently heated with stirring to 60° C. to form a second solution. This second solution is then added to the first solution with stirring until the combined solution is clear. Cooling of the second solution is not required. The combined solution is degassed under vacuum with an inert gas such as saturated argon or nitrogen. The degassing and saturating is carried out three times. Ascorbic acid is added with stirring. The final solution is degassed and saturated with the inert gas and stirred to form a clear solution.

A further embodiment of the present invention is a product made by a process described herein.

Methods of Use of Stabilized Ascorbic Acid Compositions: The present invention also provides a method of treating a condition of a subject that results from radical damage comprising administering a composition of the present invention to the subject. Treating, as used herein, means prophylactic and/or therapeutic treatment of a subject. "Prophylactic" treatment is a treatment administered to a subject who does not have symptoms of radical-induced damage or has early signs of such damage, or anticipates being exposed to situations having risk of radical-induced damage. "Therapeutic" treatment is a treatment administered to a subject who has signs of radical-induced damage. Such a condition may be photo-aging, or diseases or disorders of the skin such as skin cancer, skin irritation or inflammation, dermatitis, allergy, psoriasis, acne, eczema, rosacea, or radiation exposure, for example.

The following examples are presented to further illustrate various aspects of the present invention, and are not intended to limit the scope of the invention.

EXAMPLE 1

Stability of Ascorbic Acid Compositions Containing Cinnamic Acid Derivatives

The compositions of ascorbic acid of Table 1 were made using the following procedures: water, solvents (for Table 1: di(ethylene glycol)ethyl ether and 1,2 propanediol), phenoxyethanol, panthenol, triethanolamine and the cinnamic acid derivative were stirred together until dissolved to a clear solution. Sodium hyaluronate was sprinkled on the surface without stirring and the combination allowed to form a gel without stirring for about 3 hours. After the three hour period, the gel is stirred to obtain a uniform viscous solution. The solution is degassed under vacuum with saturated argon three times. Ascorbic acid is added with stirring, the solution degassed and saturated with argon and stirred for 30 to 45 minutes to yield a clear solution which is then degassed with saturated argon.

The stability of compositions of ascorbic acid having 0.5% by weight cinnamic acid derivatives was evaluated by using a quantitative HPLC method to measure the concentration of ascorbic acid after storage of the compositions for 4 weeks at 45° C. The HPLC method was calibrated using a known concentration of ascorbic acid. Storage for 4 weeks at 45° C. is considered equivalent to storage at room temperature for one year (*The Chemistry and Manufacture of Cosmetics*, Vol. II, pg. 9, 3$^{rd}$ edition, Michael L. Schlossman, ed., Allured Pub. Corp.). The stability of ascorbic acid is expressed as the percentage of ascorbic acid present at the end of the 4 week period based on the HPLC results.

The HPLC chromatography was carried out on an Inertsil C8 column (Chrompack, Varian, Lake Forest, Calif.) using a Waters 600E Gradient Control System (Milford, Mass.) with a mobile phase of 0.2M $KH_2PO_4$ at pH 2.4, and at a flow rate of 1 mL/min. Ascorbic acid was detected at 254 nm with a Waters 486 UV detector (Milford, Mass.). The software used for calibration and integration was Peak Simple (SR1 Instruments, Torrance, Calif.).

A visual assessment of the color of the samples at the end of 4 weeks at 45° C. was used to evaluate the degree of undesired degradation due to formation of colored products.

TABLE 1

Compositions Containing 0.5% by Weight Cinnamic Acid Derivative

| Ingredients | Amount of Ingredients in Weight % for each Composition | | | |
|---|---|---|---|---|
| | 1 | 2 | 3 | 4 |
| Water | 67.3 | 67.3 | 67.3 | 62.3 |
| Ascorbic Acid | 15.0 | 15.0 | 15.0 | 20.0 |

TABLE 1-continued

Compositions Containing 0.5% by Weight Cinnamic Acid Derivative

| Ingredients | Amount of Ingredients in Weight % for each Composition | | | |
|---|---|---|---|---|
| | 1 | 2 | 3 | 4 |
| Di(ethylene glycol) ethyl ether | 10.0 | 10.0 | 10.0 | 10.0 |
| 1,2-Propanediol | 5.0 | 5.0 | 5.0 | 5.0 |
| Phenoxyethanol | 1.0 | 1.0 | 1.0 | 1.0 |
| Panthenol | 0.5 | 0.5 | 0.5 | 0.5 |
| Triethanolamine | 0.5 | 0.5 | 0.5 | 0.5 |
| trans-Ferulic Acid | 0.5 | — | — | 0.5 |
| Caffeic Acid | — | 0.5 | — | — |
| p-Coumaric Acid | — | — | 0.5 | — |
| Sodium Hyaluronate | 0.2 | 0.2 | 0.2 | 0.2 |
| pH | 2.5–3.0 | 2.5–3.0 | 2.5–3.0 | 2.5–3.0 |
| Ascorbic Acid Stability %[1] | 84–86% | 84–86% | 88–90% | 81–83% |
| Color | pale yellow | More undesirable color than #1 | Better color than #1 | More undesirable color than #1 |

[1]the amount of ascorbic acid present at the end of a 4 week period at 45° C. as determined by calibrated HPLC Analysis of the Table 1 compositions 1, 2 and 3 indicate that p-coumaric acid has a greater stabilizing effect on ascorbic acid than does caffeic acid or trans-ferulic acid. Increased concentration of ascorbic acid (20%) in composition 4 decreases slightly the stability of ascorbic acid when compared to the data of composition 1.

Formation of color products after four weeks storage at 45° C. was also used as a criterion of ascorbic acid stability. Composition 3 containing p-coumaric acid produced a less intense pale yellow color than composition 1 that contains trans-ferulic acid. Composition 2 containing caffeic acid generated more undesirable color products than that present in composition 1.

EXAMPLE 2

Effect of Solvent on Stability of Ascorbic Acid in Compositions Containing Cinnamic Acid Derivatives The effects of solvent and solvent concentration on the stability of ascorbic acid compositions were studied using the same procedures as set forth in Example 1. Table 2 provides data comparing a control composition without di(ethylene glycol) ethyl ether with compositions 5 and 6 in which glycol ether is present at a 20% level, and where the amount of propanediol is doubled.

For compositions 5 and 6 of Table 2, the sodium hyaluronate concentration was decreased to eliminate formation of a cloudy solution that occurred in the presence of increased amounts of solvent.

TABLE 2

Effect of Solvent on Stability of Ascorbic Acid

Amount of Ingredients in Weight % for each Composition

| Ingredients | Control | 5 | 6 |
|---|---|---|---|
| Water | 77.3 | 52.4 | 52.4 |
| Di(ethylene glycol) ethyl ether | — | 20.0 | 20.0 |
| Ascorbic Acid | 15.0 | 15.0 | 15.0 |
| 1,2-Propanediol | 5.0 | 10.0 | 10.0 |
| Phenoxyethanol | 1.0 | 1.0 | 1.0 |
| Panthenol | 0.5 | 0.5 | 0.5 |
| Triethanolamine | 0.5 | 0.5 | 0.5 |
| trans-Ferulic Acid | 0.5 | 0.5 | — |
| p-Coumaric Acid | — | — | 0.5 |
| Sodium Hyaluronate | 0.2 | 0.1 | 0.1 |
| pH | 2.5–3.0 | 2.5–3.0 | 2.5–3.0 |
| Ascorbic Acid Stability %[1] | 78–80% | 92–94% | 93–95% |
| Color | yellow | very pale yellow | very pale yellow |

[1] the amount of ascorbic acid present at the end of a 4 week period at 45° C. as determined by calibrated HPLC The results of Table 2 indicate that the stability of ascorbic acid is improved in the presence of di(ethylene glycol) ethyl ether (compare compositions 5 and 6 with the control in Table 2). A comparison of the data of Table 2 with the data of Table 1 shows that the stability of ascorbic acid is increased in the presence of an increased concentration of solvents propanediol and di(ethylene glycol) ethyl ether. That is, the stability of composition 5 containing trans-ferulic acid is greater than that of composition 1 of Table 1 containing trans-ferulic acid, and the stability of composition 6 containing p-coumaric acid is greater than that of composition 3 of Table 1 containing p-coumaric acid. Increasing the concentration of the solvent, both di(ethylene glycol) ethyl ether and 1,2-propanediol, from an amount of 15% (Table 1, compositions 1–4) to an amount of 30% of the weight of the composition (Table 2, composition 6) increased the stability of the ascorbic acid.

EXAMPLE 3

Stability of Ascorbic Acid in Compositions Containing Cinnamic Acid Derivatives, Combinations Thereof, Vitamin E, and/or Detergent The present example provides data regarding compositions of ascorbic acid in the presence of increased amounts of cinnamic acid derivatives, detergent, combinations of cinnamic acid derivatives, and/or a form of Vitamin E. Table 3 provides stability results as a function of these variables.

Compositions 7–11 of Table 3 were made by mixing water, triethanolamine, cinnamic acid derivative, and panthenol until a clear solution was formed. Sodium hyaluronate was sprinkled on the surface of the solution and allowed to dissolve for about three hours to form a first solution. Separately, a mixture of di(ethylene glycol)ethyl ether, 1,2-propanediol, BRIJ® 35, phenoxyethanol, and tocopherol (for composition 11) was gently heated with stirring to 60° C. to form a second solution. The second solution was then added to the first solution with stirring until the combined solution was clear. The combined solution was degassed under vacuum and saturated with argon three times. Ascorbic acid was added with stirring. The final solution was degassed under vacuum and saturated with argon and stirred to form a clear solution.

TABLE 3

Compositions Containing Increased Concentrations of Cinnamic Acid Derivatives, Presence of Detergent, or a Tocopherol Amount of Ingredients in Weight % for each Composition

| Ingredients | 7 | 8 | 9 | 10 | 11 |
|---|---|---|---|---|---|
| Water | 46.9 | 46.9 | 47.4 | 47.4 | 63.4 |
| Di(ethylene glycol) ethyl ether | 20.0 | 20.0 | 20.0 | 20.0 | 10.0 |
| Ascorbic Acid | 15.0 | 15.0 | 15.0 | 15.0 | 15.0 |
| 1,2-Propanediol | 10.0 | 10.0 | 10.0 | 10.0 | 5.0 |
| Polyoxyethylene 23 lauryl ether (BRIJ ® 35) | 2.0 | 2.0 | 2.0 | 2.0 | 3.0 |
| Triethanolamine | 2.0 | 2.0 | 1.0 | 1.0 | 0.5 |
| trans-Ferulic Acid | 2.0 | — | 3.0 | 2.0 | 0.5 |
| p-Coumaric Acid | — | 2.0 | — | — | — |
| Caffeic Acid | — | — | — | 1.0 | — |
| Tocopherol | — | — | — | — | 1.0 |
| Phenoxyethanol | 1.0 | 1.0 | 1.0 | 1.0 | 1.0 |
| Panthenol | 1.0 | 1.0 | 0.5 | 0.5 | 0.5 |
| Sodium Hyaluronate | 0.1 | 0.1 | 0.1 | 0.1 | 0.1 |
| pH | 2.5–3.0 | 2.5–3.0 | 2.5–3.0 | 2.5–3.0 | 2.5–3.0 |
| Ascorbic Acid Stability %[1] | 82–84% | 89–91% | 83–85% | 92–94% | 88–90% |
| Color | pale yellow | pale yellow | pale yellow | pale yellow | slightly more yellow than #10 |

[1] the amount of ascorbic acid present at the end of a 4 week period at 45° C. as determined by calibrated HPLC Compositions 7, 8 and 9 containing 20% di(ethylene glycol) ethyl ether and 10% 1,2-propanediol were prepared with an increased concentration of trans-ferulic acid or p-coumaric acid as their triethanolamine salts as compared to the amounts of those acids in Tables 1 and 2. The results shown in Table 3 indicate that ascorbic acid stability decreased with increased concentration of trans-ferulic acid (2.0% and 3.0%) and p-coumaric acid (2.0%) when compared to compositions 5 and 6 of Example 2 containing 0.5% of trans-ferulic acid and 0.5% of p-coumaric acid, respectively.

The combination of 2% trans-ferulic acid and 1% caffeic acid in composition 10 provides a high stability of ascorbic acid and a low level of colored side products. The good stability further indicates that the BRIJ® 35 detergent appears not to be contributing to the lowered activity of compositions 7, 8, and 9. The stability data of composition 11, containing the additional antioxidant tocopherol, when compared to the stability results of composition 1, indicate that tocopherol increases the stability of ascorbic acid.

EXAMPLE 4

Photoprotective Effects of Stabilized Ascorbic Acid Compositions

The present example provides data showing that a combination of a cinnamic acid derivative, trans-ferulic acid, and ascorbic acid provides an unexpectedly greater photoprotective effect from UV radiation than compositions lacking such a combination.

UV irradiation: A 1000-W UV radiation (UVR) source (LIGHTNINGCURE® 200, Hamamatsu, Japan) was used for delivering solar-simulated radiation to pig skin. The lamp was combined with a dichroic mirror assembly reflecting most of the visible and infrared emission to reduce the heat load on the skin, and with a 1-mm WG295 Schott selective UVB band-pass filter (295 nm) to eliminate wavelengths less than 295 nm. A 1-cm diameter liquid light guide was connected to the exit port of the lamp housing to deliver energy to the surface of the skin. The light guide was positioned just above the surface of the skin. The intensity used in the experiment was 5 mW/cm$^2$ of UVB as measured by a research radiometer (IL1700, International Light, Newburyport, Mass.). At this irradiance, there was about 40 mW/cm$^2$ of UVA. Due to much greater erythemal effectiveness of UVB, UVB is expected to be the dominant wave band causing the observed biologic effects.

Treatment and irradiation procedure: Yorkshire pigs were clipped 24 hours before exposure. The antioxidant or vehicle formulations (500 μL) were applied to each patch of back skin (7.5 cm wide×10 cm long) daily for 4 days. One patch serves as the control and did not receive antioxidant formulation. To determine the minimal erythema dose (MED), on day three, 30 to 100 mJ/cm$^2$ at 10 mJ/cm$^2$ intervals of solar-simulated UVR was given to untreated skin. The MED was determined on day four as the lowest dose that induced perceptible erythema with distinct borders (ordinarily 40–60 mJ/cm$^2$). Also, on day four, from 1× MED to 5× MED at 1×-MED intervals of solar-simulated UVR was given in triplicate to each 7.5×10-cm area of back skin for compositions A, B, C, and E of Table 4 below. In addition, from 2× MED to 10× MED at 2× MED intervals of solar-simulated UVR was given in triplicate to each 7.5×10-cm area of back skin for compositions D and F of Table 4 below. Each treatment area was photographed using polarizing filters to minimize surface reflection. Each irradiated spot was biopsied with an 8-mm skin punch. Four biopsies of unirradiated skin were taken in each patch. Each biopsy was placed in formalin.

Measurement of erythema: By using 8–×12-inch color photographic enlargements, erythema was measured with a chromameter (COLORMOUSE® Too, Color Savvy Systems Ltd, Springboro, Ohio). Skin erythema varies appreciably depending on blood flow to the area. By photographing the area, the depth of erythema was documented at a moment in time and could be reliably measured in high-quality photographic enlargements. Three separate sites from each irradiated spot on photographs were chosen to measure the average erythemal response. Nonirradiated adjacent skin was measured for comparison. Erythema was measured in the "a*" mode as instructed by the supplier. The difference of the a* value between irradiated skin and nonirradiated skin determined the erythema.

Measurement of sunburn cells: Skin biopsy specimens were fixed in 10% neutral buffered formalin and processed for routine histology. Hematoxylin-eosin-stained center-cut sections of each biopsy specimen were analyzed for sunburn cells (keratinocytes with pyknotic nuclei having an eosinophilic cytoplasm). The entire 8-mm center section of the histologic ribbon was analyzed and the results expressed as sunburn cells/mm. When photodamage was extensive, it was difficult to precisely define a sunburn cell in the presence of epidermal necrosis. Therefore, whenever sunburn cells could not be accurately identified, an upper limit of 35 sunburn cells/mm was used.

Table 4 provides stabilized ascorbic acid compositions made as described in Example 3, applied to the skin of pigs and irradiated as described in the present example.

TABLE 4

Compositions Containing Stabilized Ascorbic Acid and Photoprotective Effects Thereof

| | Amount of Ingredients in Weight % for each Composition | | | | | |
|---|---|---|---|---|---|---|
| Ingredients | A | B | C | D$^2$ | E | F |
| Water | 79.9 | 79.4 | 64.4 | 63.4 | 78.4 | 62.3 |
| Di(ethylene glycol) ethyl ether | 10.0 | 10.0 | 10.0 | 10.0 | 10.0 | 10.0 |
| Ascorbic Acid | — | — | 15.0 | 15.0 | — | 15.0 |
| 1,2-Propanediol | 5.0 | 5.0 | 5.0 | 5.0 | 5.0 | 5.0 |

TABLE 4-continued

Compositions Containing Stabilized Ascorbic Acid and Photoprotective Effects Thereof

| Ingredients | Amount of Ingredients in Weight % for each Composition | | | | | |
|---|---|---|---|---|---|---|
| | A | B | C | D[2] | E | F |
| Polyoxyethylene 23 lauryl ether (BRIJ ® 35) | 3.0 | 3.0 | 3.0 | 3.0 | 3.0 | 3.0 |
| Triethanolamine | 0.5 | 0.5 | 0.5 | 0.5 | 0.5 | 0.5 |
| trans-Ferulic Acid | — | 0.5 | 0.5 | 0.5 | 0.5 | 0.5 |
| Tocopherol | — | — | — | 1.0 | 1.0 | 1.0 |
| Retinol | — | — | — | — | — | 1.0 |
| Phenoxyethanol | 1.0 | 1.0 | 1.0 | 1.0 | 1.0 | 1.0 |
| Panthenol | 0.5 | 0.5 | 0.5 | 0.5 | 0.5 | 0.5 |
| Sodium Hyaluronate | 0.1 | 0.1 | 0.1 | 0.1 | 0.1 | 0.1 |
| pH | 3.2 | 3.2 | 3.2 | 3.2 | 3.2 | 3.2 |
| Designation in Figures Herein | FIG. 1, FIG. 3, FIG. 4, FIG. 6, ▨ | FIG. 1, FIG. 3, FIG. 4, FIG. 6, ▤ | FIG. 1, FIG. 3, FIG. 4, FIG. 6, ■ | FIG. 2, FIG. 3, FIG. 5, FIG. 6, ▥ | FIG. 1, FIG. 3, FIG. 4, FIG. 6, ▨ | FIG. 2, FIG. 3, FIG. 5, FIG. 6, ▭ |
| Ascorbic Acid Stability %[1] | control, AA not present | control, AA not present | 84%–86% | 88%–90% | control, AA not present | ND[3] |

[1] the amount of ascorbic acid present at the end of a 4 week period at 45° C. as determined by calibrated HPLC
[2] Composition D is the same as composition 11 of Table 3.
[3] Not Determined FIG. 1, FIG. 2, and FIG. 3 provide data showing the photoprotective effect of Compositions A–F. The control (bold diagonal lines, ▨) is a measure of erythema of irradiated skin without a composition applied to the skin. The greatest photoprotective effect demonstrated in FIG. 1, i.e., the lowest colorimeter reading, was seen for the composition containing ascorbic acid and trans-ferulic acid (composition C of Table 4). Additional presence of tocopherol or tocopherol and retinol (compositions D and F of FIG. 2) enhances that protection since the colorimeter readings of FIG. 2 are at twice the minimal erythemal dose as compared to the data of FIG. 1. Data for the 2× and 4× MED exposures from FIG. 1 and FIG. 2 are combined in FIG. 3 for facilitated comparison.

Enumeration of sunburn cells in skin biopsy specimens for Compositions A–F is shown in FIG. 4, FIG. 5 and FIG. 6. The control (bold diagonal lines, ▨) is a measure of sunburned cells from irradiated skin without a composition applied to the skin. The greatest protection from photodamage demonstrated in FIG. 4, i.e., the fewest sunburn cells per millimeter, was seen for the composition containing ascorbic acid and trans-ferulic acid (composition C of Table 4). Additional presence of tocopherol or tocopherol and retinol (compositions D and F of FIG. 5) enhances that protection since the colorimeter readings of FIG. 5 are at twice the minimal erythemal dose as compared to the data of FIG. 4. Data for the 2× and 4× MED exposures from FIG. 4 and FIG. 5 are combined in FIG. 6 for facilitated comparison.

Those of skill in the art, in light of the present disclosure, will appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

As used herein and unless otherwise indicated, the terms "a" and "an" are taken to mean "one", "at least one" or "one or more".

What is claimed is:

1. A single-phase solution composition comprising by weight:
   5% to 40% L-ascorbic acid,
   0.2% to 5.0% of a cinnamic acid derivative selected from p-coumaric acid, ferulic acid, caffeic acid, sinapinic acid, combinations thereof, and cis and trans isomers thereof;
   10% to 60% of a solvent comprising a glycol ether and an alkanediol; and
   water;
   the composition having a pH of no more than about 3.5, and wherein when the cinnamic acid derivative is present at an amount greater than 0.5%, the composition further comprises a surfactant in an amount of 1.5% to 5.0%.

2. The single-phase solution composition of claim 1 wherein the cinnamic acid derivative comprises a combination of trans-ferulic acid and caffeic acid.

3. The single-phase solution composition of claim 1 wherein the cinnamic acid derivative comprises p-coumaric acid.

4. The single-phase solution composition of claim 1 wherein the cinnamic acid derivative comprises trans-ferulic acid.

5. The single-phase solution composition of claim 1 wherein the ascorbic acid is present at an amount of 10% to 20%.

6. The single-phase solution composition of claim 1 wherein the cinnamic acid derivative is present at an amount of 0.5% to 3.0%.

7. The single-phase solution composition of claim 1 wherein the glycol ether comprises di(ethylene glycol) ethyl ether.

8. The single-phase solution composition of claim 1 wherein the alkanediol comprises 1,2-propanediol.

9. The single-phase solution composition of claim 1 wherein the pH is 2.5 to 3.0.

10. The single-phase solution composition of claim 1 wherein stability of the composition is at least 88% after one year of storage, wherein stability is expressed as the percentage of ascorbic acid present.

11. The single-phase solution composition of claim 1 further comprising a form of Vitamin E and a surfactant.

12. The single-phase solution composition of claim 11 wherein the form of Vitamin E is selected from alpha, beta, delta, and gamma tocopherols, and alpha, beta, delta and gamma tocotrienols, and combinations thereof.

13. The single-phase solution composition of claim 11 wherein the form of Vitamin E is present in an amount of 0.5% to 2.0%.

14. The single-phase solution composition of claim 1 wherein the cinnamic acid derivative further comprises at least one of:
(a) substitutions on the hydroxyl groups of the aromatic ring which substitutions are selected from aliphatic groups having from one to twenty-four carbon atoms to form an ether and aliphatic groups having from one to twenty-four carbon atoms substituted with a group selected from alkyl, alkoxy, hydroxyl, amino and amido to form a substituted ether,
(b) modifications of the methoxy group(s) of the aromatic ring which modifications are selected from aliphatic groups having from two to twenty-four carbon atoms to form a long chain ether and aliphatic groups substituted with a group selected from alkyl, alkoxy, hydroxyl, amino and amido, to form a substituted long chain ether; and
(c) modifications of the 3-carboxy group which modifications are selected from esters and amides having aliphatic groups having from one to twenty-four carbon atoms or an aromatic group.

15. The single-phase solution composition of claim 11, wherein the form of Vitamin E further comprises at least one of:
(a) pharmaceutically acceptable salts thereof selected from acetate, sulfate, succinate, nicotinate, palmitate, allophanate, phosphate, quinone and halogenated salts,
(b) esters thereof,
(c) stereoisomers thereof, and
(d) substitutions and additions in the 6-chromanol ring and/or side chain thereof, with the proviso that such Vitamin E forms maintain the antioxidant activity of Vitamin E.

16. A single-phase solution composition comprising by weight:
5% to 20% L-ascorbic acid,
0.5% to 5.0% of a cinnamic acid derivative selected from p-coumaric acid, ferulic acid, caffeic acid, sinapinic acid, combinations thereof, and cis and trans isomers thereof;
10% to 60% of a solvent comprising a glycol ether and an alkanediol;
0.5% to 1.5% phenoxyethanol;
0.3% to 1.5% panthenol;
0.5% to 5.0% triethanolamine;
0.05% to 0.3% sodium hyaluronate;
1.5% to 5.0% surfactant; and
water to 100%,
the composition having a pH of no more than about 3.5.

17. The single-phase solution composition of claim 16 further comprising a form of Vitamin E in an amount of 0.3% to 2.0%.

18. The single-phase solution composition of claim 16 wherein the cinnamic acid derivative further comprises at least one of:
(a) substitutions on the hydroxyl groups of the aromatic ring which substitutions are selected from aliphatic groups having from one to twenty-four carbon atoms to form an ether and aliphatic groups having from one to twenty-four carbon atoms substituted with a group selected from alkyl, alkoxy, hydroxyl, amino and amido to form a substituted ether,
(b) modifications of the methoxy group(s) of the aromatic ring which modifications are selected from aliphatic groups having from two to twenty-four carbon atoms to form a long chain ether and aliphatic groups substituted with a group selected from alkyl, alkoxy, hydroxyl, amino and amido, to form a substituted long chain ether; and
(c) modifications of the 3-carboxy group which modifications are selected from esters and amides having aliphatic groups having from one to twenty-four carbon atoms or an aromatic group.

19. A process for stabilizing L-ascorbic acid for storage, comprising:
combining
0.2% to 0.5% of a cinnamic acid derivative selected from p-coumaric acid, ferulic acid, caffeic acid, sinapinic acid, combinations thereof, and cis and trans isomers thereof;
10% to 60% of a solvent comprising a glycol ether and an alkanediol; and
water; and
adding 5% to 40% L-ascorbic acid to form a single-phase clear solution composition of stabilized ascorbic acid, the composition having a pH of no more than about 3.5.

20. A product produced by the process of claim 19.

21. The process for stabilizing L-ascorbic acid for storage of claim 19 wherein the cinnamic acid derivative further comprises at least one of:
(a) substitutions on the hydroxyl groups of the aromatic ring which substitutions are selected from aliphatic groups having from one to twenty-four carbon atoms to form an ether and aliphatic groups having from one to twenty-four carbon atoms substituted with a group selected from alkyl, alkoxy, hydroxyl, amino and amido to form a substituted ether,
(b) modifications of the methoxy group(s) of the aromatic ring which modifications are selected from aliphatic groups having from two to twenty-four carbon atoms to form a long chain ether and aliphatic groups substituted with a group selected from alkyl, alkoxy, hydroxyl, amino and amido, to form a substituted long chain ether; and
(c) modifications of the 3-carboxy group which modifications are selected from esters and amides having aliphatic groups having from one to twenty-four carbon atoms or an aromatic group.

22. A process for stabilizing L-ascorbic acid for storage, comprising:
combining
water and 0.5% to 5.0% of a cinnamic acid derivative selected from p-coumaric acid, ferulic acid, caffeic acid, sinapinic acid, combinations thereof; and cis and trans isomers thereof, and combining
10% to 60% of a solvent comprising a glycol ether and an alkanediol, and
1.5% to 5.0% surfactant to form a second solution;

combining the first solution and the second solution to form a mixed solution; and adding 5% to 40% L-ascorbic acid to the mixed solution to form a single-phase clear solution composition of stabilized ascorbic acid, the composition having a pH of no more than about 3.5.

23. A product produced by the process of claim 22.

24. The process for stabilizing L-ascorbic acid for storage of claim 22 wherein the cinnamic acid derivative further comprises at least one of:
(a) substitutions on the hydroxyl groups of the aromatic ring which substitutions are selected from aliphatic groups having from one to twenty-four carbon atoms to form an ether and aliphatic groups having from one to twenty-four carbon atoms substituted with a group selected from alkyl, alkoxy, hydroxyl, amino and amido to form a substituted ether,
(b) modifications of the methoxy group(s) of the aromatic ring which modifications are selected from aliphatic groups having from two to twenty-four carbon atoms to form a long chain ether and aliphatic groups substituted with a group selected from alkyl, alkoxy, hydroxyl, amino and amido, to form a substituted long chain ether; and
(c) modifications of the 3-carboxy group which modifications are selected from esters and amides having aliphatic groups having from one to twenty-four carbon atoms or an aromatic group.

25. A method of treating a subject for effects of radical-induced damage, comprising:
administering to the subject a stabilized single-phase solution composition comprising by weight:
5% to 40% L-ascorbic acid,
0.2% to 5.0% of a cinnamic acid derivative selected from p-coumaric acid, ferulic acid, caffeic acid, sinapinic acid, combinations thereof, and cis and trans isomers thereof;
10% to 60% of a solvent comprising a glycol ether and an alkanediol; and
water;
the composition having a pH of no more than about 3.5, and wherein when the cinnamic acid derivative is present at greater than 0.5%, the composition further comprises a surfactant in an amount of 1.5% to 5.0%.

26. The method of claim 25 wherein the stabilized single-phase solution composition comprises a cinnamic acid derivative at greater than 0.5% and the composition further comprises a form of Vitamin E.

27. The method of claim 26 wherein the form of Vitamin E is selected from alpha, beta, delta, and gamma tocopherols, and alpha, beta, delta and gamma tocotrienols, and combinations thereof.

28. The method of claim 25 wherein the cinnamic acid derivative comprises a combination of trans-ferulic acid and caffeic acid.

29. The method of claim 25 wherein the cinnamic acid derivative comprises p-coumaric acid.

30. The method of claim 25 wherein the cinnamic acid derivative comprises trans-ferulic acid.

31. The method of claim 25 wherein the ascorbic acid is present at an amount of 10% to 20%.

32. The method of claim 25 wherein the cinnamic acid derivative is present at an amount of 0.5% to 3.0%.

33. The method of claim 25 wherein the glycol ether comprises di(ethylene glycol) ethyl ether.

34. The method of claim 25 wherein the alkanediol comprises 1,2-propanediol.

35. The method of claim 25 wherein the pH of the composition is 2.5 to 3.0.

36. The method of claim 27 wherein the form of Vitamin E is present in an amount of 0.5% to 2.0%.

37. The method of treating a subject for effects of radical-induced damage of claim 25, wherein the cinnamic acid derivative further comprises at least one of:
(a) cinnamic acid derivatives having substitutions on the hydroxyl groups of the aromatic ring which substitutions are selected from aliphatic groups having from one to twenty-four carbon atoms to form an ether and aliphatic groups having from one to twenty-four carbon atoms substituted with a group selected from alkyl, alkoxy, hydroxyl, amino and amido to form a substituted ether,
(b) cinnamic acid derivatives having modifications of the methoxy group(s) of the aromatic ring which modifications are selected from aliphatic groups having from two to twenty-four carbon atoms to form a long chain ether and aliphatic groups substituted with a group selected from alkyl, alkoxy, hydroxyl, amino and amido, to form a substituted long chain ether; and
(c) cinnamic acid derivatives having modifications of the 3-carboxy group which modifications are selected from esters and amides having aliphatic groups having from one to twenty-four carbon atoms or an aromatic group.

38. A method of treating the skin of a subject for effects of radical-induced damage, comprising:
administering to the skin of the subject a stabilized single-phase solution composition comprising by weight,
5% to 20% L-ascorbic acid,
0.5% to 5.0% of a cinnamic acid derivative selected from p-coumaric acid, ferulic acid, caffeic acid, sinapinic acid, combinations thereof, and cis and trans isomers thereof;
10% to 60% of a solvent comprising a glycol ether and an alkanediol;
0.5% to 1.5% phenoxyethanol;
0.3% to 1.5% panthenol;
0.5% to 5.0% triethanolamine;
0.05% to 0.3% sodium hyaluronate;
0.3% to 2.0% of a form of Vitamin E,
1.5% to 5.0% of a surfactant, and
water to 100%, the composition having a pH of no more than about 3.5.

39. The method of claim 38 wherein the single-phase solution composition further comprises an antioxidant selected from (a) a Vitamin A derivative selected from retinoid, retinol, retinal, retinoic acid, a retinoic acid salt and mixtures thereof, (b) lipoic acid, (c) seleno-L-methionine, and (d) flavonoids that lack undesirable color.

40. The method of treating the skin of a subject for effects of radical-induced damage of claim 38, wherein the cinnamic acid derivative further comprises at least one of:
(a) cinnamic acid derivatives having substitutions on the hydroxyl groups of the aromatic ring which substitutions are selected from aliphatic groups having from one to twenty-four carbon atoms to form an ether and aliphatic groups having from one to twenty-four carbon atoms substituted with a group selected from alkyl, alkoxy, hydroxyl, amino and amido to form a substituted ether,
(b) cinnamic acid derivatives having modifications of the methoxy group(s) of the aromatic ring which modifications are selected from aliphatic groups having from two to twenty-four carbon atoms to form a long chain ether and aliphatic groups substituted with a group selected from alkyl, alkoxy, hydroxyl, amino and amido, to form a substituted long chain ether; and
(c) cinnamic acid derivatives having modifications of the 3-carboxy group which modifications are selected from esters and amides having aliphatic groups having from one to twenty-four carbon atoms or an aromatic group.

41. A method of treating the skin of a subject for effects of radical-induced damage, comprising:
administering to the skin of the subject a stabilized single-phase solution composition comprising by weight,
5% to 40% L-ascorbic acid;
0.5% to 5.0% of a cinnamic acid derivative selected from p-coumaric acid, ferulic acid, caffeic acid, sinapinic acid, combinations thereof, and cis and trans isomers thereof;
10% to 60% of a solvent comprising a glycol ether and an alkanediol;
0.5% to 1.5% phenoxyethanol;
0.3% to 1.5% panthenol;
0.5% to 5.0% triethanolamine;
0.05% to 0.3% sodium hyaluronate;
0.3% to 2.0% of a form of Vitamin E;
1.5% to 5.0% of a surfactant;
0.3% to 2.0% retinol; and
water to 100%,
the composition having a pH of no more than about 3.5.

42. The method of treating the skin of a subject for effects of radical-induced damage of claim 41, wherein the cinnamic acid derivative further comprises at least one of:
(a) cinnamic acid derivatives having substitutions on the hydroxyl groups of the aromatic ring which substitutions are selected from aliphatic groups having from one to twenty-four carbon atoms to form an ether and aliphatic groups having from one to twenty-four carbon atoms substituted with a group selected from alkyl, alkoxy, hydroxyl, amino and amido to form a substituted ether,
(b) cinnamic acid derivatives having modifications of the methoxy group(s) of the aromatic ring which modifications are selected from aliphatic groups having from two to twenty-four carbon atoms to form a long chain ether and aliphatic groups substituted with a group selected from alkyl, alkoxy, hydroxyl, amino and amido, to form a substituted long chain ether; and
(c) cinnamic acid derivatives having modifications of the 3-carboxy group which modifications are selected from esters and amides having aliphatic groups having from one to twenty-four carbon atoms or an aromatic group.

* * * * *